(12) United States Patent
Redoules et al.

(10) Patent No.: US 6,569,906 B1
(45) Date of Patent: May 27, 2003

(54) COMPOSITION CONTAINING A PRECURSOR CAPABLE OF BEING HYDROLYSED BY GLUCOCEREBROSIDASE

(75) Inventors: Daniel Redoules, Toulouse (FR); Roger Tarroux, Toulouse (FR); Jean-Jacques Perie, Castanet (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 0 days.

(21) Appl. No.: 09/856,220

(22) PCT Filed: Mar. 9, 1999

(86) PCT No.: PCT/FR99/00521

§ 371 (c)(1),
(2), (4) Date: Jan. 15, 2002

(87) PCT Pub. No.: WO99/46273

PCT Pub. Date: Sep. 16, 1999

(30) Foreign Application Priority Data

Mar. 10, 1998 (FR) .............................. 98 02888

(51) Int. Cl.[7] ...................... A61K 31/045; A61K 31/05
(52) U.S. Cl. ...................... 514/738; 514/731; 514/451; 514/452; 536/120; 536/43; 536/4.1; 536/18.6; 568/716

(58) Field of Search ........................... 536/120, 43, 4.1, 536/18.6; 514/738, 731, 451, 452; 568/716

(56) References Cited

U.S. PATENT DOCUMENTS

| | | | | | |
|---|---|---|---|---|---|
| 5,972,993 | A | * | 10/1999 | Ptchelintsev | ................. 514/449 |
| 6,071,543 | A | * | 6/2000 | Thornfeldt | .................. 424/642 |
| 6,335,023 | B1 | * | 1/2002 | Yu et al. | ..................... 424/401 |
| 6,437,004 | B1 | * | 8/2002 | Perricone | .................... 514/738 |

* cited by examiner

*Primary Examiner*—Samuel Barts
*Assistant Examiner*—Devesh Khare
(74) *Attorney, Agent, or Firm*—The Firm of Hueschen and Sage

(57) ABSTRACT

The invention concerns a composition capable of being hydrolyzed by a cutaneous enzyme, glucocerebrosidase. The active precursor is advantageously a gluco-conjugate derived from phenol whereof the two α carbons are free. The invention also concerns the use of such compositions against light-induced skin ageing or for making a medicine for treating certain skin diseases. The invention further concerns novel glucosylated compounds.

15 Claims, No Drawings

COMPOSITION CONTAINING A PRECURSOR CAPABLE OF BEING HYDROLYSED BY GLUCOCEREBROSIDASE

The present invention relates to a cosmetic or pharmaceutical composition for skin application, containing a compound capable of releasing a biologically active substance in contact with the skin through the action of an enzyme of the skin surface: glucocerebrosidase.

The expression "precursor of an active agent" is understood to mean a conjugated compound of an inactive molecule with a biologically active substance. A precursor of an active agent has no inherent biological activity (or has a low activity), and releases, once metabolized, said active substance in the stratum corneum. A "derivative of an active agent" is distinguishable from a "precursor of an active agent" in that it is endowed with an inherent biological activity.

The use of precursors of active agents in cosmetology is a common practice, in particular for enhancing the stability of the active agents in the compositions and/or for facilitating the penetration of the active agents into the epidermis.

Precursors of vitamins are widely used in this regard.

Indeed, vitamins are difficult to formulate because of their high instability to air and to heat.

Vitamin derivatives having a structure similar to the active molecule and whose stability would be improved were first proposed. These derivatives have nevertheless proved to have excessively low activities.

Precursors of vitamins, such as esters of fatty acids, esters of glycerides, phosphates or sulfates of vitamins, are preferred to them.

The fatty acid esters of an active agent, such as vitamin E palmitate (or alpha-tocopherol palmitate), have the advantage not only of stabilizing the active agent but also of enhancing the skin penetration of a water-soluble active agent by increasing its affinity for the lipophilic stratum corneum.

Patent application FR-2 715 565 describes a composition containing two precursors which release the same active agent according to two different kinetics through a synergetic mechanism. The precursors are chosen from phosphates, sulfates, palmitates, propionates, acetates, ferulates, ethers, amides and glycosidic derivatives of active agents.

The compositions given as examples contain two precursors of vitamin C: phosphated vitamin C and glucosylated vitamin C. These two precursors interact with two different enzymes, a phosphatase and a glucosidase, to release vitamin C in a synergetic manner.

Patent application EP-487 404 describes the use of a glucosylated precursor of vitamin C (or ascorbic acid) for preparing a dermatological composition which exerts a vitamin C activity in the body. This application describes in particular alpha-glucolsyl-L-ascorbic acids, which have no inherent activity and which are hydrolyzed to glucose and to L-ascorbic acid by a cutaneous enzyme.

Some glycosidic derivatives of active agents, which themselves have a biological activity, have already been described.

In the context of a study on tocopherols (EP-169 716), it has been demonstrated that the glucosylated derivatives of delta-tocopherol have an anti-allergic activity. Patent JP-60 56 994 describes the antioxidant activity of dl-alpha-tocopherylglucose, dl-alpha-tocopherylgalactose and d-delta-tocopherylgalactose. The activity of these glucosylated derivatives of tocopherol has nevertheless proved insufficient such that their use as a biologically active substance is of little interest.

The object of the present invention is to provide a composition for skin application which releases an active agent according to a kinetics such that the concentration of active agent in the epidermis remains greater than the biologically active concentration, but less than the pro-inflammatory concentration.

The applicant has indeed demonstrated that conventional cosmetic compositions containing an active agent such as vitamin E generate a pro-inflammatory effect. This pro-inflammatory effect is the consequence of a superactivity of the active agent at the concentration used. This is all the more problematic as the concentration used is necessary in order to observe the desired biological effects.

To avoid any excessive concentration of the active agent in the period following skin application of the composition, the applicant proposes using a precursor of an active agent which is capable of being hydrolyzed by an enzyme whose kinetics meets the two criteria set out above.

The applicant has demonstrated that glucocerebrosidase makes it possible to solve the problem posed.

It is known that the inhibition of glucocerebrosidase by topical treatment with bromo-condutirol-B-epoxide causes acute barrier function disruptions (Holleran W. M., Elias P. M., "Permeability barrier requirements regulate epidermal β-glucocerebrosidase", J. Lipid. Res., 1994, 35, 905–912).

These results demonstrate that, on the one hand, this enzyme is accessible via the topical route and, on the other hand, that it plays an essential role in the equilibrium of the cutaneous system.

Furthermore, glucocerebrosidase exhibits a high activity in the stratum corneum: the natural substrates of this enzyme, glucocerebrosides, are hydrolyzed to ceramides which represent 40% by weight of the lipids in the stratum corneum (Lampe M. A., Williams M. L. and Elias P. M., "Human epidermal lipids: characterization and modulation during differentiation", J. Lipid. Res., 24, 131–140).

The applicant has demonstrated, by clinical studies carried out on 22 patients, that the activity of glucocerebrosidase varies little as a function of the depth of the horny layer and varies little as a function of the individuals and of the season. Glucocerebrosidase is therefore a hydrolase with a high and constant activity.

The applicant has, in addition, demonstrated that the kinetics of glucocerebrosidase hydrolysis makes it possible to envisage the use of a precursor of an active agent which releases the active agent at a rate which is both sufficient to ensure its activity and moderate to avoid any intolerance due to an excessive concentration of the active agent.

Accordingly, the subject of the present invention is a cosmetic or pharmaceutical composition for skin application containing a compound capable of releasing a biologically active substance in contact with the skin through the action of a cutaneous enzyme, characterized in that the enzyme is glucocerebrosidase.

The expression "compound capable of releasing a biologically active substance" is understood to mean a compound having a structure similar to a natural substrate of said enzyme.

According to a preferred embodiment, the compound capable of releasing the biologically active substance is a conjugated compound of said substance with a carbohydrate such that:

said biologically active substance has a phenol residue in which the two carbons at the alpha position of the phenol functional group are unsubstituted, and the chemical linkage between said biologically active substance and said carbohydrate is an ether functional group between the carbohydrate and the phenol functional group of the biologically active substance.

In order to facilitate the penetration of the precursor of an active agent into the stratum corneum, the biologically active substance advantageously exhibits a lipophilic character.

The carbohydrate is a C3–C6 monosaccharide such as glucose, mannose, galactose, preferably glucopyranose or one of its derivatives.

The biologically active substance may be a therapeutically active substance chosen from tioxolone, paracetamol, oxyphenylbutazone, isoxsuprine, etilefrine, p-pentyloxyphenol, delta-tocopherol, tocol and flavonoids.

The formula for the compounds listed is given below.

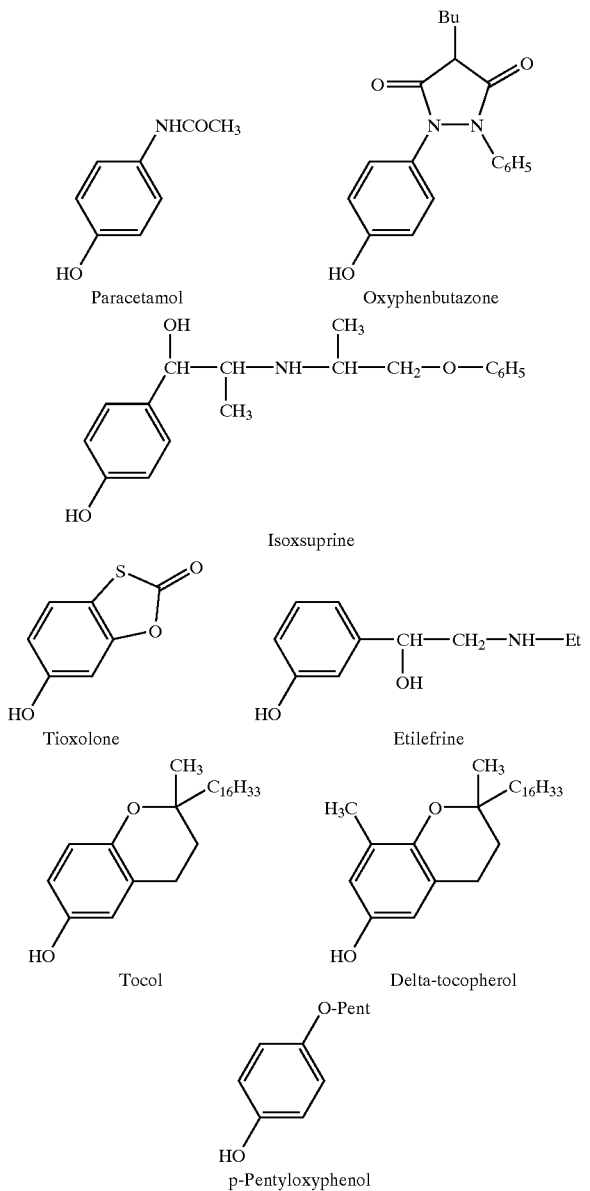

Paracetamol corresponds to p-acetamidophenol. In the formulae for tocol and delta-tocopherol, $C_{16}H_{33}$ at the 2-position of the 3,4-dihydrobenzopyran is 4,8,12-trimethyltridecyl substituent.

The biologically active substance may have an action strictly at the level of the epidermis, in particular when it is chosen from tocol, delta-tocopherol, flavonoids (which are antioxidants) and tioxolone (which is an anti-seborrheic agent).

The biologically active substance may also have a broader action at the level of the epidermis or at another level in the body: paracetamol is an analgesic, oxyphenbutazone an anti-inflammatory agent, isoxsuprine a vasodilator, etilefrine a hypotensive agent and p-pentyloxyphenol a bactericidal agent.

The present invention also relates to the conjugated compounds of a biologically active substance with a carbohydrate such that:

said biologically active substance, different from delta-tocopherol, has a phenol residue in which the two carbons at the alpha position of the phenol functional group are unsubstituted, and the chemical linkage between said biologically active substance and said carbohydrate is an ether functional group between the carbohydrate and the phenol functional group of the biologically active substance.

The preferred compounds in the context of the present invention are such that the carbohydrate is C3–C6 monosaccharide, in particular glucose.

The compounds are chosen from tioxonyl-glucopyranoside, oxyphenbutazonyl-glucopyranoside, p-acetamidophenyl-glucopyranoside, isoxsuprinyl-glucopyranoside, etilefrinyl-glucopyranoside, p-pentyloxyphenyl-glucopyranoside and tocol-glucopyranoside.

The compositions according to the invention containing a compound capable of releasing tocol, delta-tocopherol or a flavonoid are effective against skin aging, against drying of the skin or for soothing the effects due to exposure to solar radiation and to pollutants, or against the production of free radicals which are responsible for cutaneous oxidative stress.

Cutaneous oxidative stress leads to the production of various molecules such as conjugated dienes, which are generated from polyunsaturated fatty acids, malonaldehyde and tumidine glycol obtained from oxidative attack of the genome. Natural antioxidants, such as tocopherol or synthetic antioxidants, such as tocol, make it possible to combat the deleterious effects of free radicals and peroxides on cutaneous supramolecular edifices.

The applicant has demonstrated that, under mild oxidation conditions, the direct application of these antioxidants to the skin causes nevertheless pro-inflammatory effects which are the consequence of superactivity at the concentrations commonly used.

The compositions of the invention advantageously make it possible to overcome this pro-inflammatory effect by providing a precursor of an active agent whose biological activity is very low or even zero, and which is slowly hydrolyzed by glucocerebrosidase to generate the active antioxidant after application of the composition to the skin. The slow release of the active agent ensures better bioavailability of the active agent in the cutaneous medium and a more effective protection.

The present invention also relates to the use of the compositions containing a compound capable of releasing delta-tocopherol, tocol or a flavonoid, for the manufacture of a medicament intended for the treatment of certain skin diseases, in particular atopic dermatitis, acne or psoriasis.

The precursors of an active agent or conjugated compounds according to the invention may be obtained by a biochemical method or by organic synthesis. According to a method of organic synthesis, the active agent is coupled to the carbohydrate, previously tetraacylated and activated at the 1-position (epimeric carbon) with an imidate. The acetyl groups are then hydrolyzed by methanolate ions.

The compositions according to the invention contain from 0.001 to 10% by weight, preferably 0.01% by weight, of a precursor of an active agent relative to the total weight of the composition.

The composition according to the invention may be provided in the form of an oil-in-water (O/W) or water-in-oil (W/O) emulsion. It may also be provided in the form of spherules such as liposomes, nanocapsules or nanospheres. When the composition is an emulsion, the proportion of the fatty phase ranges from 5 to 80% by weight, preferably from 5 to 50% by weight, relative to the total weight of the composition. The oils, the emulsifiers and the coemulsifiers used in the composition, in the form of an emulsion, are chosen from those conventionally used in cosmetics. The emulsifier and the coemulsifier are present in the composition in a proportion ranging from 0.3 to 10% by weight, relative to the total weight of the composition.

The composition according to the invention may also contain acceptable cosmetic or dermatological additives. These additives may be in particular surfactants, fatty substances, moisturizing agents, preservatives, perfumes, gelling agents, chelators, pigments such as TiO2, screening agents and free vitamins such as ascorbic acid.

The present invention will be illustrated without limitation by the following examples.

COMPARATIVE EXAMPLE 1

Demonstration of the Pro-inflammatory Effect of a Nonconjugated Active Agent in a Cream Rich in a Polyunsaturated Fatty Acid of the Prior Art The concentration of malonaldehyde (MDA) released in a cream containing increasing quantities of an antioxidant, vitamin E (or alpha-tocopherol), which is subjected to an oxidative stress, is measured. It should be recalled that the quantity of MDA released, a good indicator of the activity of free radicals, is inversely proportional to the efficacy of an antioxidant.

The cream containing vitamin E also contains borage oil which is naturally rich in linoleic acid. Oxidative stress consists in a two hour solar exposure.

The concentration of MDA released is measured by complexing with thiobarbituric acid in an acidic medium. The chromogenic complex formed absorbs at 532 nm. Its quantification is monitored by fluorimetry.

The following table shows that the higher increase in the concentration of vitamin E, the higher the quantity of MDA released. Quite obviously, vitamin E causes a pro-inflammatory effect in a cream rich in polyunsaturated fatty acid.

| Concentration of vitamin E in the cream (% by mass) | Concentration of MDA released ($\mu$g MDA/100 mg cream) |
| --- | --- |
| 0 | 0.7 ± 0.06 |
| 0.05 | 1.2 ± 0.15 |
| 0.1 | 1.9 ± 0.20 |
| 0.15 | 2.0 ± 0.20 |

EXAMPLE 2

Demonstration of the Very Low Activity of the Glucoconjugates of the Invention Compared with that of the Free Active Agents The antioxidant activity of various compounds against the peroxidation of an unsaturated lipid, squalene, is measured. The activity indicator chosen is MDA as in example 1.

The table below summarizes the results obtained.

| Compound | Quantity of MDA released ($\mu$g MDA) |
| --- | --- |
| Tocol | 6 ± 1.9 |
| Delta-tocopherol | 7.2 ± 1.7 |
| Vitamin E palmitate | 182.7 ± 39 |
| Delta-tocopherol-glucopyranoside | 128 ± 38 |
| Tocol-glucopyranoside | 142 ± 28 |

The precursors of active agents, such as delta-tocopheryl-glucopyranoside or tocol-glucopyranoside, posses a low antioxidant power comparable to that of esters of vitamin E, such as vitamin E palmitate. On the other hand, once hydrolyzed to delta-tocopherol and to tocol, respectively, the antioxidant activity is revealed.

EXAMPLE 3

Stability of the Precursors of Active Agents According to the Invention

The photostability of delta-tocopheryl-glucopyranoside and that of delta-tocopherol are compared.

Samples of a cream containing 0.4% of delta-tocopheryl-glucopyranoside or of delta-tocopherol are irradiated with a 28 J/cm$^2$ incident light of 290 to 800 nm (5 DEM).

The following table shows that the glucosylated precursors of an active agent are at least twice as photostable as the active agents which they may release.

| Compound | | Micromoles |
| --- | --- | --- |
| Delta-tocopherol | Irradiated | 88 ± 15 |
| | Nonirradiated | 310 ± 14 |
| Delta-tocopherol-glucopyranoside | Irradiated | 208 ± 4 |
| | Nonirradiated | 311 ± 7 |

EXAMPLE 4

Kinetics of Hydrolysis of Glucosylated Precursors with Glucocerebrosidase

The precursor and the stratum corneum sample in powdered form are incorporated into a liquid medium buffered with a phthalate buffer at pH 5.6. The mixture is incubated for 24 hours and the quantity of active agent released is assayed by densitometry on a thin-layer chromatography plate.

The following table gives, for various glucosylated precursors, the quantity of molecule released following their hydrolysis by glucocerebrosidase over 24 hours by a freeze-dried cutaneous extract obtained after taking a sample by three successive strippings of 15 cm$^2$.

| Glucosylated precursors | Molecule released | Quantity of molecule released (n mol/hour) |
| --- | --- | --- |
| 4-methylumbelliferyl-glucopyranoside | 4-Methylumbelliferone (reference substrate) | 100 ± 7 |

-continued

| Glucosylated precursors | Molecule released | Quantity of molecule released (n mol/hour) |
|---|---|---|
| α-Tocopheryl-glucopyranoside | α-Tocopherol | 0 |
| γ-Tocopheryl-glucopyranoside | γ-Tocopherol | 0 |
| δ-Tocopheryl-glucopyranoside | δ-Tocopherol | 14.3 ± 1 |
| Tocol-glucose | Tocol | 14.8 ± 1.2 |
| Phenylglucopyranoside | Phenol | 0.2 ± 0.5 |

As regards the kinetics of release of the δ-tocopherol and tocol derivatives, they are 7 times as low as those of the reference derivative (4-methylumbelliferyl glucopyranoside) used for assaying the activity of β-glucocerebrosidase and therefore makes it possible to obtain some effects over time.

It is observed that α-tocopherol and γ-tocopherol are not released and remain in the form of a precursor because of their bulkiness in the vicinity of the C-1 linkage.

In the following examples, the proportions are in percentage by mass:

EXAMPLE 5

| | |
|---|---|
| Delta-tocopheryl-beta-dl-glucopyranoside or tocol-beta-dl-glucopyranoside | 0.01 |
| Liquid paraffin | 20 |
| Squalene | 5 |
| Octyl palmitate | 20 |
| PEG-40 stearate | 2 |
| Preservative | 0.2 |
| Perfume | 0.15 |
| Glycerine | 5 |
| Water QS | 100 |

EXAMPLE 6

| | |
|---|---|
| Delta-tocopheryl-beta-dl-glucopyranoside or tocol-beta-dl-glucopyranoside | 0.01 |
| Natural borage oil | 20 |
| Liquid paraffin | 10 |
| PEG-40 stearate | 4 |
| Preservative | 0.2 |
| Perfume | 0.15 |
| Glycerine | 10 |
| Water QS | 100 |

What is claimed is:

1. A cosmetic or pharmaceutical composition for skin application containing a compound capable of releasing a biologically active substance in contact with the skin through the action of a cutaneous enzyme, wherein the enzyme is glucocerebrosidase.

2. A composition of claim 1, wherein the compound capable of releasing the biologically active substance is a conjugated compound of the biologically active substance with a carbohydrate such that:

the biologically active substance has a phenol residue in which the two carbons at the alpha position of the phenol functional group are unsubstituted, and the chemical linkage between the biologically active substance and the carbohydrate is an ether functional group between the carbohydrate and the phenol functional group of the biologically active substance.

3. A composition of claim 2, wherein the carbohydrate is a 6-carbon monosaccharide.

4. A composition of claim 2, wherein the monosaccharide is glucopyranose or a glucopyranose derivative.

5. A composition of claim 1, wherein the biologically active substance is lipophilic.

6. A composition of claim 1, wherein the biologically active substance is a therapeutically active substance selected from tioxolone, paracetamol, oxyphenylbutazone, isoxsuprine, etilefrine, and p-pentyloxyphenol.

7. A composition of claim 1, wherein the biologically active substance is selected from delta-tocopherol, tocol and flavonoids.

8. A composition of claim 7, useful against skin aging, against drying of the skin, against the production of free radicals, or for soothing the effects due to exposure to solar radiation or pollutants.

9. A method of treating a living animal body afflicted with a skin disease, comprising the step of administering to the living animal body an amount of a compound of claim 7 which is effective for alleviation of the skin disease.

10. A method of claim 9, wherein the skin disease is selected from atopic dermatitis, acne, and psoriasis.

11. A composition of claim 1 wherein the composition contains 0.001 to 10% by weight of the composition capable of releasing the biologically active substance, relative to the total weight of the composition.

12. A conjugated compound of a biologically active substance with a carbohydrate such that:

the biologically active substance, different from delta-tocopherol, has a phenol residue in which the two carbons at the alpha position of the phenol functional group are unsubstituted, and the chemical linkage between the biologically active substance and the carbohydrate is an ether functional group between the carbohydrate and the phenol functional group of the biologically active substance.

13. A compound of claim 12, wherein the carbohydrate is a 6-carbon monosaccharide.

14. A compound of claim 13, selected from tioxonyl-glucopyranoside, oxyphenbutazonyl-glucopyranoside, p-acetamidophenyl-glucopyranoside, isoxsuprinyl-glucopyranoside, etilefrinyl-glucopyranoside, p-pentyloxyphenyl-glucopyranoside and tocol-glucopyranoside.

15. A compound of claim 12, wherein the monosaccharide is glucose.

* * * * *

UNITED STATES PATENT AND TRADEMARK OFFICE
CERTIFICATE OF CORRECTION

PATENT NO.     : 6,569,906 B1                              Page 1 of 1
DATED          : May 27, 2003
INVENTOR(S)    : Daniel Redoules et al.

It is certified that error appears in the above-identified patent and that said Letters Patent is hereby corrected as shown below:

<u>Title page,</u>
Item [86], US filing date: "January 15, 2002" should be -- May 18, 2001 --.

Signed and Sealed this

Sixteenth Day of September, 2003

JAMES E. ROGAN
*Director of the United States Patent and Trademark Office*